(12) United States Patent
Saralya et al.

(10) Patent No.: US 8,283,499 B2
(45) Date of Patent: Oct. 9, 2012

(54) PREPARATION OF NAPHTHOQUINONE COMPOUNDS USING 2,3-DIHALONAPHTHOQUINONE

(75) Inventors: Sanjay Sukumar Saralya, Bangalore (IN); Shashikumar Hiriyalu Somashekar, Bangalore (IN); Shashiprabha, Bangalore (IN); Shridhara Kanakamajalu, Bangalore (IN); Koottungalmadhom Ramaswamy Ranganathan, Bangalore (IN); Veerasamy Ananthalakshmi, Bangalore (IN); Govindarajalu Jeyaraman, Bangalore (IN); Kothapalli Sundarraja Rao, Bangalore (IN); Kuppuswamy Nagarajan, Bangalore (IN)

(73) Assignee: Alkem Laboratories Limited, Mumbai (IN)

( * ) Notice: Subject to any disclaimer, the term of this patent is extended or adjusted under 35 U.S.C. 154(b) by 219 days.

(21) Appl. No.: 12/921,096

(22) PCT Filed: Mar. 6, 2009

(86) PCT No.: PCT/IN2009/000158
§ 371 (c)(1),
(2), (4) Date: Sep. 3, 2010

(87) PCT Pub. No.: WO2009/122432
PCT Pub. Date: Oct. 8, 2009

(65) Prior Publication Data
US 2011/0004024 A1    Jan. 6, 2011

(30) Foreign Application Priority Data
Mar. 7, 2008 (IN) ............................ 473/MUM/2008

(51) Int. Cl.
*C07C 45/48* (2006.01)
*C07C 49/747* (2006.01)

(52) U.S. Cl. .................... 568/310; 568/314; 568/328
(58) Field of Classification Search .................. 568/310, 568/314, 328
See application file for complete search history.

(56) References Cited

U.S. PATENT DOCUMENTS

| | | | | |
|---|---|---|---|---|
| 2,553,647 A | * | 5/1951 | Fieser et al. | 552/298 |
| 3,367,830 A | * | 2/1968 | Sarett | 514/681 |
| 7,847,127 B2 | * | 12/2010 | Kumar et al. | 568/310 |

OTHER PUBLICATIONS

Fieser et al. Naphthoquinone Antimalarials. II. Correlation of Structure and Activity Against P. Iophurae in Ducks. Journal of the American Chemical Society, 1948, vol. 70, 3156-3165.*

* cited by examiner

*Primary Examiner* — Sikarl Witherspoon
(74) *Attorney, Agent, or Firm* — George W. Moxon, II; Brian P. Harrod

(57) ABSTRACT

The present invention relates the use of 2,3-dihalonaphthoquinone compounds of Formula I

FORMULA (I)

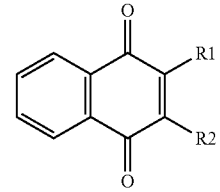

wherein $R^1$ and $R^2$ are leaving groups like halogens selected from the group comprising Cl, Br, I and F and the $R^1$ and $R^2$ may be the same halogen or may contain different halogen groups, or sulphonyl groups, for making napthoquinone compounds of Formula IA

FORMULA (IA)

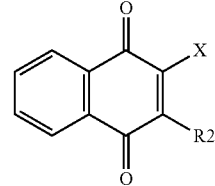

wherein X is any aryl, heteroaryl, alkyl, cyclohexyl, substituted cylohexyl groups and the like.

11 Claims, No Drawings

PREPARATION OF NAPHTHOQUINONE COMPOUNDS USING 2,3-DIHALONAPHTHOQUINONE

FIELD OF THE INVENTION

The present invention relates to preparation of napthoquinone compounds by using a 2,3-dihalonapthoquinone intermediate.

BACKGROUND OF THE INVENTION

A wide range of naphthoquinones are known in the art. Such compounds have been variously described as having antimalarial, anticoccidial and antitheilerial activity. Some compounds have also been described as possessing activity against external parasites. Thus, Fieser et al, J. Amer. Chem. Soc. 1948, 70, 3156-3165 (and references cited therein) describes a large number of 2-substituted-3-hydroxy-1,4-naphthoquinones as having antimalarial activity. A number of these compounds have also been described in U.S. Patent Specification No. 2553647 and 2553648. Further classes of 2-substituted-3-hydroxy-1,4-naphthoquinones having activity as antimalarial, anticoccidial and/or antitheilerial agents are described in U.S. Pat. Nos. 3367830, and 3347742, U.K. Patent Specification No. 1553424, and European Patent Specifications Nos. 2228, 77551, 77550 and 123,238.

European Patent No. 123,238 discloses 2-substituted-3-hydroxy-1,4-naphthoquinones which are said to be active against the human malaria parasite *Plasmodium falciparum* and also against *Eimeria* species such as *E. tenella* and *E. acervulina*, which are causative organisms of coccidiosis. 2-Substituted-3-hydroxy-1,4-naphthoquinones(1) have been described in literature as possessing anti-protozoal activity, in particular anti-malarial. Anti-coccicidal activity has also been reported to a lesser extent. Hundreds of such compounds as possessing anti-malarial activity have been disclosed by Fieser and co-workers. All these compounds use 2-chloro-1,4-naphthoquinone (2) as one of the starting materials.

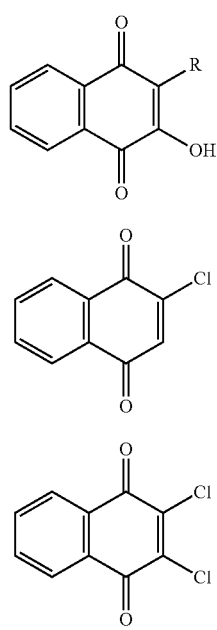

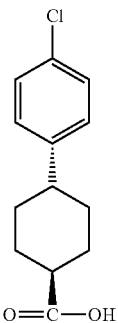

Synthesis of 2-chloro-1,4-naphthoquinone in the laboratory always resulted in a mixture of monochloro and dichloronaphthoquinone i.e. 2-Chloro and 2,3-Dichloronaphthoquinones. Material procured from market was also found to contain almost 10-12% of 2,3-dichloronaphthoquinone(3). The preparation of pure 2-chloronaphthoquinone from this material is tedious and results in loss, making it expensive. Prior art has used the condensation of trans-4-(4-chlorophenyl)cyclohexanecarboxylic acid(4) with 2-chloro-1,4-naphthoquinone(2) to give 2-chloro-3-[trans-4-(4-chlorophenyl)cyclohexyl]-1,4-naphthoquinone(5) which on hydrolysis yielded Atovaquone (6) which is a very well known antimalerial drug. We have however surprisingly found that condensation of trans-4-(4-chlorophenyl)cyclohexanecarboxylic acid (4) with the abundantly available, commercially inexpensive 2,3-dichloronaphthoquinone(3) gave an improved yield of 2-chloro-3-[trans-4-(4-chlorophenyl)cyclohexyl]-1,4-naphthoquinone(5) which on hydrolysis yielded Atovaquone(6). We report for the first time these reactions and their commercial applications which are hitherto unknown.

OBJECT OF THE INVENTION

It is an object of the present invention to provide the use of 2,3-dihalonaphthoquinone compounds of Formula I for the preparation of napthoquinone compounds of Formula IA.

It is further object of the present invention to provide a process for preparation of napthoquinone compounds of Formula IA comprising 2-cyclohexyl-3-halo-1,4-naphthoquinones or substituted cyclohexyl derivatives thereof, which may be used to prepare 2-cyclohexyl-1,4-naphthoquinones compounds of Formula III and their geometric/structural isomers.

It is further object of the present invention to provide the condensation of 2,3-dichloro-1,4-naphthoquinone of formula (3) with trans 4-(4-chlorophenyl)cyclohexane-1-carboxylic acid of formula (4) in acetonitrile in presence of silver nitrate and ammonium persulfate in a suitable solvent to provide 2-[4-(4- chlorophenyl)cyclohexyl]-3-chloro-1,4-naphthoquinone of formula (5); and treating 2-[4-(4-chlorophenyl)cyclohexyl]-3-chloro-1,4-naphthoquinone of formula (5) with base in a solvent and followed by treatment with acid to provide Atovaquone of formula (6).

It is further object of the present invention to provide a process comprising
a) condensing 2,3-dichloro-1,4-naphthoquinone of formula (3) with trans 4-(4-chlorophenyl)cyclohexane-1-carboxylic acid of formula (4) in acetonitrile in presence of silver nitrate and ammonium persulfate in a suitable solvent to provide 2-[4-(4-chlorophenyl)cyclohexyl]-3-chloro-1,4-naphthoquinone of formula (5);
b) recovery and reuse of acetonitrile from the mother liquors; since the above process uses large quantity of acetonitrile which is an expensive solvent and has become scarce now a days.

c) recovery and reuse of silver salt by further conversion to silver nitrate; since silver nitrate also is an expensive material and contribute significantly to the cost. The fate of silver from the above reaction is not known in any of the prior arts, we have found out for the first time the nature of the silver salt and conversion of the salt to silver nitrate and reuse of the same in the reaction.

d) treating 2-[4-(4-chlorophenyl)cyclohexyl]-3-chloro-1, 4-naphthoquinone of formula (5) with base in a solvent and followed by treatment with acid to provide Atovaquone of formula (6).

It is further object of the present invention to provide atovaquone form I of at least 99% purity by using a combination of solvents. Prior art uses large quantity of acetonitrile for recrystallisation of atovaquone to get form I. Commercially this is not viable and the large quantity of the solvent usage is a bottleneck in manufacturing. Surprisingly we have found that considerably small quantity of combination of solvents produce form I and the output from the reactor can be enhanced significantly.

All the objects are met in part or whole by the current process wherein 2,3-dihalonaphthoquinone compounds of Formula I are used to prepare napthoquinone compounds of Formula IA, which may be further used to prepare 2-cyclohexyl-1,4-naphthoquinones compounds of Formula III such as Atovaquone of formula (6), Parvaquone of formula (8) and 2-trans-(4-t-Butylcyclohexyl)-3-hydroxy-1,4-naphthoquinone of formula (10). Industrially feasible, economical, and environmentally benign processes have been developed for the preparation of above products.

SUMMARY OF THE INVENTION

According to one aspect of the present invention is provided the use of 2,3-dihalonaphthoquinone compounds of Formula I

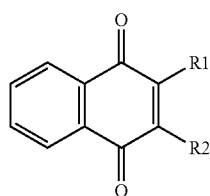

FORMULA (I)

wherein $R^1$ and $R^2$ are leaving groups like halogens selected from the group comprising Cl, Br, I and F and the $R^1$ and $R^2$ may be the same halogen or may contain different halogen groups, or sulphonyl groups for making napthoquinone compounds of Formula IA

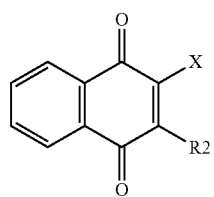

FORMULA (IA)

wherein X is any aryl, heteroaryl, alkyl cyclohexyl, substituted cyclohexyl groups and the like thereof.

According to another aspect of the present invention is provided a process for the preparation of 2-cyclohexyl-1,4-naphthoquinones compounds of Formula III and its isomers,

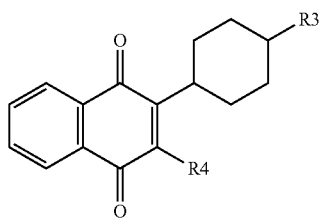

FORMULA (III)

wherein, $R^3$ is selected from the group comprising $C_{1-6}$alkoxy; aralkoxy; $C_{1-6}$alkyl-$C_{1-6}$alkoxy; hydrogen; unsubstituted phenyl; phenyl substituted by one or more groups, preferably selected from halogens; $C_{1-6}$ linear or branched alkyl, halogen and perhalo-$C_{1-6}$ alkyl; $R^4$ is selected from the group comprising hydroxyl; a group $OCOR^5$, wherein $R^5$ is a $C_{1-10}$alkyl group, a $C_{3-10}$ cycloalkyl group, a $C_{1-10}$ alkoxy group, or a phenyl or naphthyl group, each such $R^5$ group being optionally substituted e.g. by amino, mono or di-$C_{1-4}$ alkylamino, carboxy or hydroxy; a group $OR^6$ or $SR^6$, wherein $R^6$ is an optionally substituted $C_{1-10}$ alkyl, $C_{3-10}$ cycloalkyl, phenyl or naphthyl group as defined for $R^5$ or a group $NR^7R^8$, wherein $R^7$ and $R^8$ each independently represent hydrogen or $C_{1-4}$ alkyl, or the group $NR^7R^8$ which represents a 5-7 membered saturated heterocyclic ring, which may optionally contain a further heteroatom selected from nitrogen, oxygen or sulphur; and physiologically acceptable salts and other physiologically functional derivatives thereof, comprising the steps of:
(i) using 2,3-dihalonaphthoquinone compounds of Formula I

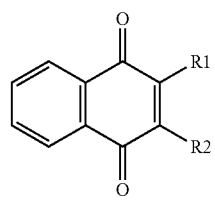

FORMULA (I)

wherein $R^1$ and $R^2$ are leaving groups like halogens selected from the group comprising Cl, Br, I and F and the $R^1$ and $R^2$ may be the same halogen or may contain different halogen groups, or sulphonyl groups, to prepare napthoquinone compounds of Formula IA;

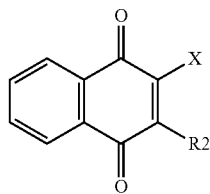

FORMULA (IA)

wherein X is any aryl, heteroaryl, alkyl, cyclohexyl, substituted cylohexyl groups and the like thereof;

(ii) using napthoquinone compounds of Formula IA in a suitable solvent to further prepare the said 2-cyclohexyl-1,4-naphthoquinones compounds of Formula III and their geometric/structural isomers.

It is to be noted that the Formula IA will cover the stereoisomers including geometrical and optical isomers of the compounds disclosed above.

The napthoquinone compounds of Formula IA comprising 2-cyclohexyl-3-halo-1,4-naphthoquinones or substituted cyclohexyl derivatives thereof, may then be used to prepare 2-cyclohexyl-1,4-naphthoquinones compounds of Formula III and its geometrical isomers,

FORMULA (III)

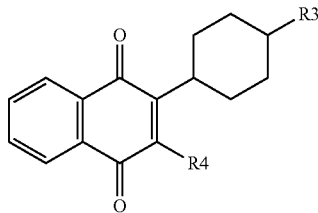

Wherein $R^3$ is defined as above and $R^4$ is selected from the group comprising hydroxyl; a group $OCOR^5$, wherein $R^5$ is a $C_{1-10}$ alkyl group, a $C_{3-10}$ cycloalkyl group, a $C_{1-10}$ alkoxy group, or a phenyl or naphthyl group, each such $R^5$ group being optionally substituted e.g. by amino, mono or di-$C_{1-4}$ alkylamino, carboxy or hydroxy; a group $OR^6$ or $SR^6$, wherein $R^6$ is an optionally substituted $C_{1-10}$ alkyl, $C_{3-10}$ cycloalkyl, phenyl or naphthyl group as defined for $R^5$ or a group $NR^7R^8$, wherein $R^7$ and $R^8$ each independently represent hydrogen or $C_{1-4}$ alkyl, or the group $NR^7R^8$ represents a 5-7 membered saturated heterocyclic ring, which may optionally contain a further heteroatom selected from nitrogen, oxygen or sulphur; and physiologically acceptable salts and other physiologically functional derivatives thereof.

The invention may be summarized as given below:

A. The use of 2,3-dihalonaphthoquinone compounds of Formula I

FORMULA (I)

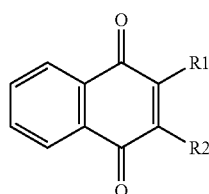

wherein $R^1$ and $R^2$ are leaving groups like halogens selected from the group comprising Cl, Br, I and F and the $R^1$ and $R^2$ may be the same halogen or may contain different halogen groups, or sulphonyl groups, for making napthoquinone compounds of Formula IA

FORMULA (I)

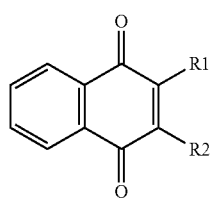

wherein X is any aryl, heteroaryl, alkyl, cyclohexyl, substituted cylohexyl groups and the like.

B. A process for the preparation of 2-cyclohexyl-1,4-naphthoquinones compounds of Formula III and its isomers,

FORMULA (III)

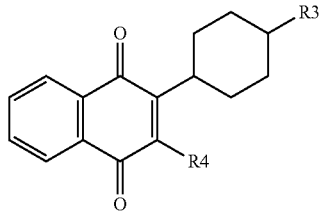

wherein, $R^3$ is selected from the group comprising $C_{1-6}$ alkoxy; aralkoxy; $C_{1-6}$ alkyl-$C_{1-6}$ alkoxy; hydrogen; unsubstituted phenyl; phenyl substituted by one or more groups, preferably selected from halogens; $C_{1-6}$ linear or branched alkyl, halogen and perhalo-$C_{1-6}$ alkyl; $R^4$ is selected from the group comprising hydroxyl; a group $OCOR^5$, wherein $R^5$ is a $C_{1-10}$ alkyl group, a $C_{3-10}$ cycloalkyl group, a $C_{1-10}$ alkoxy group, or a phenyl or naphthyl group, each such $R^5$ group being optionally substituted e.g. by amino, mono or di-$C_{1-4}$ alkylamino, carboxy or hydroxy; a group $OR^6$ or $SR^6$, wherein $R^6$ is an optionally substituted $C_{1-10}$ alkyl, $C_{3-10}$ cycloalkyl, phenyl or naphthyl group as defined for $R^5$ or a group $NR^7R^8$, wherein $R^7$ and $R^8$ each independently represent hydrogen or $C_{1-4}$ alkyl, or the group $NR^7R^8$ which represents a 5-7 membered saturated heterocyclic ring, which may optionally contain a further heteroatom selected from nitrogen, oxygen or sulphur; and physiologically acceptable salts and other physiologically functional derivatives thereof, comprising the steps of:

(i) using 2,3-dihalonaphthoquinone compounds of Formula I

FORMULA (I)

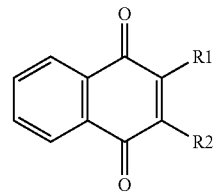

wherein $R^1$ and $R^2$ are leaving groups like halogens selected from the group comprising Cl, Br, I and F and the $R^1$ and $R^2$ may be the same halogen or may contain different halogen groups, or sulphonyl groups, to prepare napthoquinone compounds of Formula IA;

FORMULA (IA)

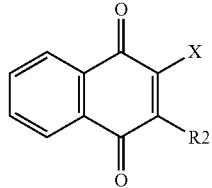

wherein X is any aryl, heteroaryl, alkyl, cyclohexyl, substituted cylohexyl groups and the like;

(ii) using napthoquinone compounds of Formula IA in a suitable solvent to further prepare the said 2-cyclohexyl-1,4-naphthoquinones compounds of Formula III or their geometric/structural isomers.

C. A process for the preparation of Atovaquone of formula (6),

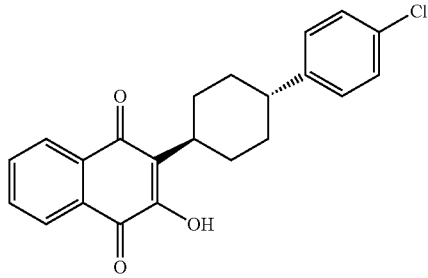

Formula (6)

comprising the steps of:

(i) condensing 2,3-dichloro-1,4-naphthoquinone of formula (3)

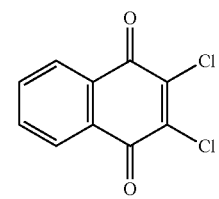

Formula (3)

with trans 4-(4-chlorophenyl)cyclohexane-1-carboxylic acid of formula (4)

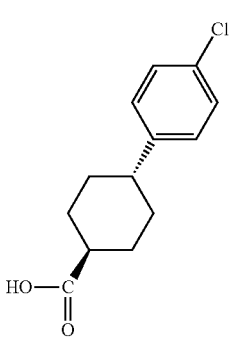

Formula (4)

in presence of silver nitrate and ammonium persulfate in a suitable solvent to provide 2-[4-(4-chlorophenyl)cyclohexyl]-3-chloro-1,4-naphthoquinone of formula (5),

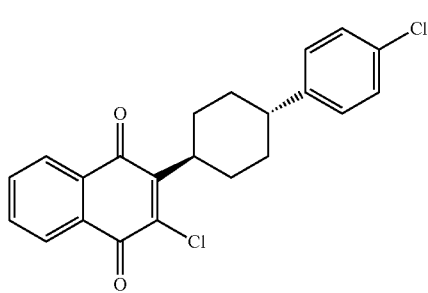

Formula (5)

(ii) treating 2-[4-(4-chlorophenyl)cyclohexyl]-3-chloro-1,4-naphthoquinone of formula (5) with a base in a solvent and followed by treatment with an acid to provide Atovaquone of formula (6).

D. Process as in step C above, wherein the process comprises:

a) condensing 2,3-dichloro-1,4-naphthoquinone of formula (3) with trans 4-(4-chlorophenyl)cyclohexane-1-carboxylic acid of formula (4) in acetonitrile in presence of silver nitrate and ammonium persulfate in a suitable solvent to provide 2-[4-(4-chlorophenyl)cyclohexyl]-3-chloro-1,4-naphthoquinone of formula (5);

b) recovery and reuse of acetonitrile from the mother liquor c) recovery of silver salt and further conversion to silver nitrate and its reuse;

d) treating 2-[4-(4-chlorophenyl)cyclohexyl]-3-chloro-1,4-naphthoquinone of formula (5) with base in a solvent and followed by treatment with an acid to provide Atovaquone of formula (6).

E. Process as in step C above, wherein the acid used for acidification is selected from an organic acid selected from the group comprising aliphatic acids and aromatic acids, sulphonic acids or mixtures thereof and the like.

F. Process as in step E above, wherein the acid is acetic acid.

G. Process as in step C above, wherein the atovaquone is dissolved in N-methylpyrrolidone and precipitated by adding acetonitrile to obtain atovaquone polymorph Form I.

H. Process as in step C above, wherein the process comprises using silver nitrate and 2,3-dihalonaphthoquinone in the molar ratio of 0.8:1 to 2:1 to provide atovaquone form I of at least 99% purity.

I. A process for the preparation of Parvaquone of formula (8),

Formula (8)

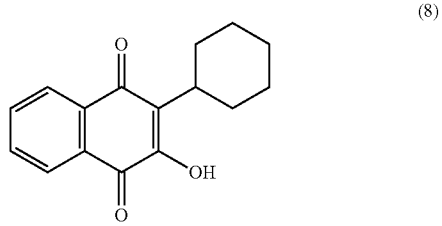

(8)

which comprises the steps of (i) condensing 2,3-dichloro-1,4-naphthoquinone of formula (3)

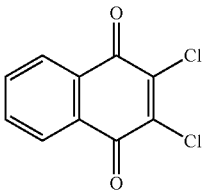

Formula (3)

with 4- cyclohexane carboxylic acid in presence of silver nitrate and ammonium persulfate in a suitable solvent to provide 2-Cyclohexyl 3-chloro 1:4-naphthoquinone of formula (7),

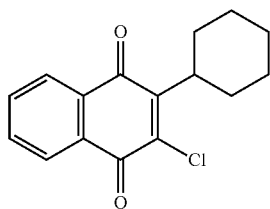

Formula (7)

(ii) treating 2-cyclohexyl-3-chloro-1,4-naphthoquinone of formula (7) with base in a solvent followed by treatment with an acid to provide Parvaquone of formula (8).

J. A process for the preparation of 2-trans-(4-t-Butylcyclohexyl)-3-hydroxy-1,4-naphthoquinone of formula (10),

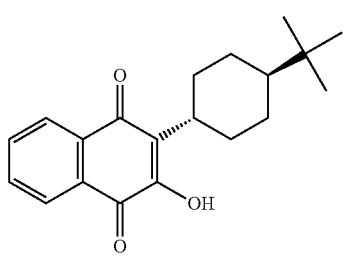

Formula (10)

which comprises the steps of (i) condensing 2,3-dichloro-1,4-naphthoquinone of formula (3)

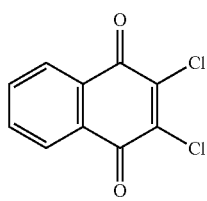

Formula (3)

with 1-trans-(4-t-butyl-cyclohexyl)-carboxylic acid in presence of silver nitrate and ammonium persulfate in a suitable solvent to provide 2-trans-(4-t-butylcyclohexyl)-3-chloro-1,4-naphthoquinone of formula (9),

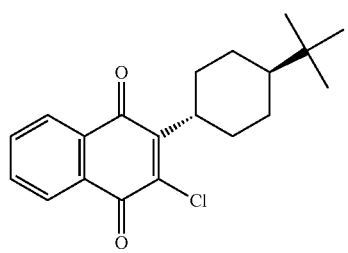

Formula (9)

(ii) treating 2-trans-(4-t-butylcyclohexyl)-3-chloro-1,4-naphthoquinone of formula (9) with base in a solvent and followed by treatment with an acid to provide 2-trans-(4-t-butylcyclohexyl)-3-hydroxy-1,4-naphthoquinone of formula (10).

K. Process as in step B above, wherein the solvent is selected from the group comprising substituted, unsubstituted, cyclic, bicyclic, saturated, or unsaturated, straight or branched hydrocarbon but not limited to aliphatic or aromatic hydrocarbon, having $C_6$-$C_{10}$ atoms, water, aliphatic nitrile, alcohols, ketones, esters, ethers and chlorinated solvents, or mixtures thereof L. Process as in step K above, wherein the solvent is selected from the group comprising hexane, toluene; esters such as ethyl acetate, propyl acetate, isopropyl acetate, butyl acetate and isobutyl acetate; water; aliphatic nitrile such as acetonitrile and propionitrile; alcohols such as methanol, ethanol and isopropanol; ketones such as acetone, methyl ethyl ketone, methyl isobutyl ketone and diethyl ketone; ethers such as tetrahydrofuran and dioxane; and chlorinated solvents such as methylene chloride, chloroform, carbontetrachloride and ethylene dichloride; and the like or mixtures thereof.

BRIEF DESCRIPTION OF DRAWING FIGURES

Further objects of the present invention together with additional features contributing thereto and advantages accruing there from will be apparent from the following description of preferred embodiments of the invention which are shown in the accompanying drawing figures wherein:

Table 1 gives the details of observation that acidification of the reaction mass by organic acids, especially acetic acid removes majority of the impurities and to provide pure material of purity not less than 99.0%.

Table 2 describes details of yield of Atovaquone by using the various ratio of 2,3-Dichloro 1,4-napthoquinone (3) and 2-Chloro-1,4-naphthoquinone.

DESCRIPTION OF THE INVENTION

Before the present process and methods are described, it is to be understood that this invention is not limited to particular compounds, formulas or steps described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a compound" includes a plurality of such compounds and reference to "the step" includes reference to one or more step and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In accordance with the present invention, there is provided a process for preparation of napthoquinone compounds by using a 2,3-dihalonapthoquinone intermediate. More specifically the invention is concerned with the use of novel intermediate 2,3-dihalonapthoquinone (Formula I) for the preparation of napthoquinone compounds of Formula IA preferably selected from 2-cyclohexyl-3-halo-1,4-naphthoquinones or substituted cyclohexyl derivatives thereof The napthoquinone compounds of Formula IA may then be used for preparation of 2-cyclohexyl-1,4-naphthoquinones compounds of Formula III.

In accordance with the present invention, there is provided the use of 2,3-dihalonaphthoquinone compounds of Formula I, wherein $R^1$ and $R^2$ are halogens selected from the group comprising Cl, Br, I and F and the $R^1$ and $R^2$ may be the same halogen or may contain different halogen groups.

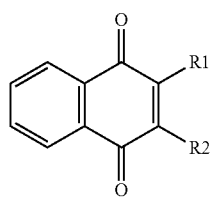

FORMULA (I)

A particularly preferred example of the compound of Formula I is 2,3-dichloro naphthoquinone.

In accordance with the present invention, there is provided a use of 2,3-dihalonaphthoquinone compounds of Formula I for the preparation of napthoquinone compounds of Formula IA,

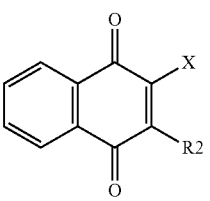

FORMULA (IA)

Wherein X is any aryl, heteroaryl, alkyl, cylohexyl and substituted cyclohexyl groups and the like.

Particularly the present invention provides the use of 2,3-dihalonaphthoquinone compounds of Formula I for the preparation of napthoquinone compounds of Formula IA.

Preferred compounds of Formula IA may be selected from the compounds of Formula II given below, and may be preferably selected from 2-cyclohexyl-3-halo-1,4-naphthoquinones or substituted cyclohexyl derivatives thereof.

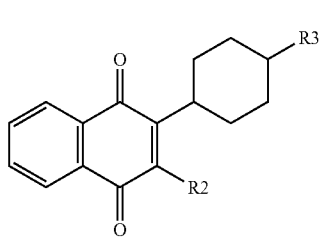

FORMULA (II)

wherein $R^2$ is defined as above and $R^3$ is selected from the group comprising $C_{1-6}$alkoxy; aralkoxy; $C_{1-6}$alkyl-$C_{1-6}$alkoxy; hydrogen; sulphonyl, unsubstituted phenyl; phenyl substituted by one or more groups, preferably selected from halogens; $C_{1-6}$ linear or branched alkyl, halogen and perhalo-$C_{1-6}$ alkyl.

It is to be noted that the compounds of Formula IA and Formula II will cover the stereoisomers including geometrical and optical isomers of the compounds disclosed above.

Some non-limiting examples of compounds of Formula IA and II include:
2-[trans-4-(4-Chlorophenyl)cyclohexyl]-3-chloro-1,4-naphthoquinone;
2-Cyclohexyl-3-chloro-1,4-naphthoquinone, and
2-trans-(4-t-Butylcyclohexyl)-3-chloro-1,4-naphthoquinone.

The napthoquinone compounds of Formula IA and II, may then be used to prepare 2-cyclohexyl-1,4-naphthoquinones compounds of Formula III.

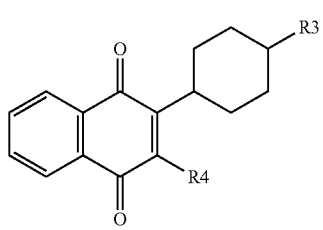

FORMULA (III)

wherein $R^3$ is defined as above and $R^4$ is selected from the group comprising hydroxyl; a group $OCOR^5$, wherein $R^5$ is a $C_{1-10}$alkyl group, a $C_{3-10}$ cycloalkyl group, a $C_{1-10}$alkoxy group, or a phenyl or naphthyl group, each such $R^5$ group being optionally substituted e. g. by amino, mono-or di-$C_{1-4}$alkylamino, carboxy or hydroxy; a group $OR^6$ or $SR^6$, wherein $R^6$ is an optionally substituted $C_{1-10}$alkyl, $C_{3-10}$cycloalkyl, phenyl or naphthyl group as defined for $R^5$; or a group $NW^7R^8$, wherein $R^7$ and $R^8$ each independently represent hydrogen or $C_{1-4}$ alkyl, or the group $NW^7R^8$ represents a 5-7 membered saturated heterocyclic ring, which may optionally contain a further heteroatom selected from nitrogen, oxygen or sulphur; and physiologically acceptable salts and other physiologically functional derivatives thereof.

Some non-limiting examples of compounds of Formula III include:
2-[trans-4-(4-Chlorophenyl)cyclohexyl]-3-hydroxy-1,4-naphthoquinone (Atovaquone);
2-Cyclohexyl-3-hydroxy 1,4-naphthoquinone (Parvaquone) and;
2-trans-(4-t-Butylcyclohexyl)-3-hydroxy-1,4-naphthoquinone.

The 2,3-dihalonaphthoquinone compound of Formula I is treated with a cyclohexane carboxylic acid or any substituted derivative thereof in the presence of silver nitrate and ammonium persulphate to give the napthoquinone compounds of Formula IA selected from 2-cyclohexyl-3-halo-1,4-naphthoquinones or substituted cyclohexyl derivatives thereof Molar ratios of the of the reactants were varied and good results (~40% yield) were obtained when 2,3-dihalonaphtaquinone, cyclohexylcarboxyllic acid or its substituted derivatives and silver nitrate were used in approximately equimolar ratio whereas in the prior arts the molar ratio used are in the range of 0.3 to 0.7 molar equivalents of silver nitrate with respect to naphthaquinone which gave very low (less than 20%) yields. In a preferred embodiment of the process of the present invention, silver nitrate and 2,3-dihalonaphthoquinone were used in the molar ratio of 0.8:1 to 2:1. Using the reactants in the above molar ratio provided atovaquone form I of at least 99% purity.

The napthoquinone compounds of Formula IA, may be further converted to 2-cyclohexyl-1,4-naphthoquinones compounds of Formula III using various reagents known in the art. For example the napthoquinone compounds of Formula IA may be hydrolyzed with potassium hydroxide and acidified with hydrochloric acid to give 2-cyclohexyl-3-hydroxyl-1,4-naphthoquinones compounds. The product so obtained contains lot of impurities, some of which are more polar than atovaquone and some which are less polar. It is difficult to remove these impurities without significant yield loss and in the prior art, this has been achieved by crystallizing from excess of acetonitrile. Surprisingly it is observed that acidification of the reaction mass by acids such as organic acids like aliphatic acids or aromatic acids or mixtures thereof removes majority of the impurities and provides pure material of purity not less than 99.0%. Preferably organic acids such as acetic acid are used in this step. The following table illustrates the observations.

TABLE 1

| Impurities/ Atovaquone | RT (min) for the impurities/Atovaquone | Acetic acid acidification (Product composition area %) | Hydrochloric acid acidification (Product composition area %) |
| --- | --- | --- | --- |
| Impurity # 1 | 4.5 | 0.09 | 0.12 |
| Impurity # 2 | 5.28 | 0.35 | 0.32 |
| Impurity # 3 | 10.64 | 0.08 | 0.10 |
| Impurity # 4 | 13.52 | 0.15 | 1.55 |
| Impurity # 5 | 17.46 | 0.26 | 0.03 |
| Atovaquone | 20.23 | 99.00 | 97.80 |

Acetonitrile from the above reaction mother liquor is recovered in amounts more than 80% and reused for the reaction without the loss of yield and quality of the product. Similarly silver salt is recovered, characterized by XRD as silver chloride and converted back into silver nitrate to a substantial extent and reused with out the loss of yield and purity of the product. This reduces the effluent load and also improves the economy of the process at large-scale manufacturing purposes.

Particularly preferred compounds for use according to the present invention includes use of 2,3-dichloronaphthoquinone for the preparation of 2-chloro-3-trans-[4-(4-chlorophenyl)cyclohexyl]-1,4-naphthoquinone and subsequently preparation of 2-[trans-4-(4-chlorophenyl)cyclohexyl]-3-hydroxy-1,4-naphthoquinone (Atovaquone). In the course of our investigations on the synthesis of Atovaquone (6) we found surprisingly that the condensation of trans-4-(4-chlorophenyl)cyclohexane carboxylic acid (4) with the abundantly available, commercially inexpensive 2,3-dichloronaphthoquinone (3) in the presence of silver nitrate and ammonium perdisulphate gave a reasonable yield of 2-chloro-3-trans-[4-(4-chlorophenyl)cyclohexyl]-1,4-naphthoquinone (5) which on hydrolysis yielded Atovaquone (6). Since position 3 in 2,3-dichloronaphthoquinone was occupied by a chlorine atom, it was not anticipated that it would be displaced by a substituted cyclohexyl group. This surprising finding led us to a systematic study of the reaction using pure 2,3-dichloro naphthoquinone (3) and different mixtures of this with 2-chloronaphthoquinone (2). Table 2 summarizes the results with yields of 2-chloro-3-trans-[4-(4-chlorophenyl)cyclohexyl]-1,4-naphthoquinone (5) and Atovaquone (6). The table shows clearly that mixtures of 2,3-dichloro naphthoquinone (3) and 2-chloro-1,4-naphthoquinone (2), particularly in the range of 9:1 to 1:9 gave better yields of 2-chloro-3-trans-[4-(4-chlorophenyl)cyclohexyl]-1,4-naphthoquinone (5) and hence of Atovaquone (6) when compared to the use of 2-chloronaphthoquinone (2) or 2,3-dichloronaphthoquinone (3) alone. Since the preparation of pure 2-chloronaphthoquinone goes through a crude product which contains at least 10% 2,3-dichloronaphthoquinone, the process of our invention allows the direct use of this crude mixture.

TABLE 2

| S. No. | Quantity of 2,3-Dichloro 1,4-napthoquinone (3) | Quantity of 2-Chloro-1,4-naphthoquinone (2) | Ratio % Wt./wt. | Yield of (5) | Yield of Atovaquone (6) |
| --- | --- | --- | --- | --- | --- |
| 1 | 5.0 gm | — | +98% | 1.5 gm | 0.999 gm |
| 2 | 4.5 gm | 0.5 gm | 90:10 | 2.0 gm | 1.334 gm |
| 3 | 3.5 gm | 1.5 gm | 70:30 | 2.0 gm | 1.334 gm |
| 4 | 2.5 gm | 2.5 gm | 50:50 | 2.1 gm | 1.400 gm |
| 5 | 1.5 gm | 3.5 gm | 30:70 | 2.0 gm | 1.334 gm |
| 6 | 0.5 gm | 4.5 gm | 10:90 | 2.0 gm | 1.334 gm |
| 7 | — | 5.0 gm | +98% | 1.25 gm | 0.833 gm |

The 2,3-dichloronaphthoquinone was found to give a product with lesser impurities, for example, from the 2-chloronaphthoquinone reaction, the solid product obtained from the reaction was found to consist of 55-75% of the trans isomer(5), 10-20% of the cis-isomer and 3-7% of an unknown impurity. On the other hand, the solid product from the reaction using 2,3-dichloronaphthoquinone had >90% of the trans isomer (5), <2% of the cis isomer and none of the unknown impurity. The improved purity profile of the latter had a considerable impact on the manufacture of (5). Further 2,3-dichloronaphthoquinone being a significantly cheaper raw material, it becomes an excellent source for the production of 2-[trans-4-(4-chlorophenyl)cyclohexyl]-3-hydroxy-1,4-naphthoquinone (Atovaquone).

In accordance with the present invention, said reaction is carried out in the solvent selected from the group comprising substituted, unsubstituted, cyclic, bicyclic, saturated, or unsaturated, straight or branched hydrocarbon but not limited to aliphatic or aromatic hydrocarbon, having $C_6$-$C_{10}$ atoms, water, aliphatic nitrile, alcohols, ketones, esters, ethers and chlorinated solvents, or mixtures thereof The solvent used in the present invention is selected from the group consisting of hexane, toluene; esters such as ethyl acetate, propyl acetate, isopropyl acetate, butyl acetate and isobutyl acetate; water; aliphatic nitrile such as acetonitrile and propionitrile; alcohols such as methanol, ethanol and isopropanol; ketones such as acetone, methyl ethyl ketone, methyl isobutyl ketone and diethyl ketone; ethers such as tetrahydrofuran and dioxane; and chlorinated solvents such as methylene chloride, chloroform, carbontetrachloride and ethylene dichloride; and the like or mixtures thereof The above said solvents may also used for process of preparing Atovaquone form I in one or more solvents of a first type and/or one or more antisolvent of a second type to get polymorph Form I In another embodiment of the present invention, there is provided a process for preparation of polymorph Form I which is obtained by using much less quantity of solvents by dissolving the crude atovaquone obtained from the above process in n-methylpyrrolidone and precipitating quantitatively the product by adding acetonitrile as antisolvent. Pharmacetically pure atovaquone was obtained in the original patent by crystallizing crude atovaquone from excess of acetonitrile. The crystals so obtained are considered to be polymorphic form I, as referred in patent WO2006008752 (Tarur et. al.). By following the present process, Atovaquone is obtained with all the related substances well within the desired limits. A few crystals of atovaquone of form I can also be added optionally to the antisolvent.

In another embodiment of the present invention, there is provided a process for the preparation of Parvaquone of formula (8), Formula (8)

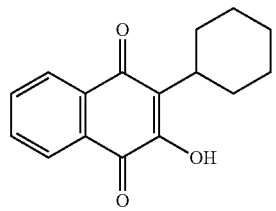

(8)

which comprises the steps of (i) a)condensing 2,3-dichloro-1,4-naphthoquinone of formula (3)

Formula (3)

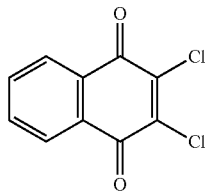

with cyclohexane carboxylic acid in presence of silver nitrate and ammonium persulfate in a suitable solvent to provide 2-Cyclohexyl 3-chloro 1:4-naphthoquinone of formula (7), b) recovery and reuse of acetonitrile from the mother liquor, c) recovery of silver salt and further conversion to silver nitrate and its reuse;

Formula (7)

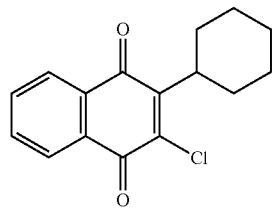

(ii) treating 2-cyclohexyl-3-chloro-1,4-naphthoquinone of formula (7) with base in a solvent followed by treatment with an acid to provide Parvaquone of formula (8).

In another embodiment of the present invention, there is provided a process for the preparation of 2-trans-(4-t-Butyl-cyclohexyl)-3-hydroxy-1,4-naphthoquinone of formula (10), Formula (10)

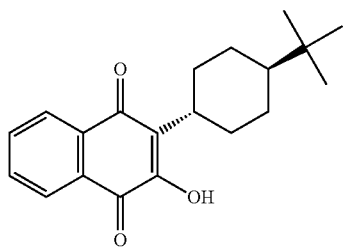

which comprises the steps of (i) a)condensing 2,3-dichloro-1,4-naphthoquinone of formula ($^3$)

Formula (3)

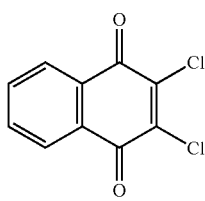

with 1-trans-(4-t-butyl-cyclohexyl)-carboxylic acid in presence of silver nitrate and ammonium persulfate in a suitable solvent to provide 2-trans-(4-t-butylcyclohexyl)-3-chloro-1,4-naphthoquinone of formula (9), Formula (9)

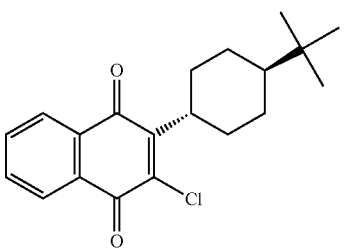

b) recovery and reuse of acetonitrile from the mother liquor, c) recovery of silver salt and further conversion to silver nitrate and its reuse;

(ii) treating 2-trans-(4-t-butylcyclohexyl)-3-chloro-1,4-naphthoquinone of formula (9) with base in a solvent followed by treatment with an acid to provide 2-trans-(4-t-butylcyclohexyl)-3-hydroxy-1,4-naphthoquinone of formula (10).

The following examples are intended to illustrate the scope of the present invention in all its aspects but not to limit it thereto.

EXAMPLE 1

1.2-[trans-4-(4-Chlorophenyl)cyclohexyl]-3-hydroxy-1,4-naphthoquinone (Atovaquone):

Stage I: Synthesis of 2-[trans-4-(4-chlorophenyl)cyclohexyl]-3-chloro-1,4-naphthoquinone (5)

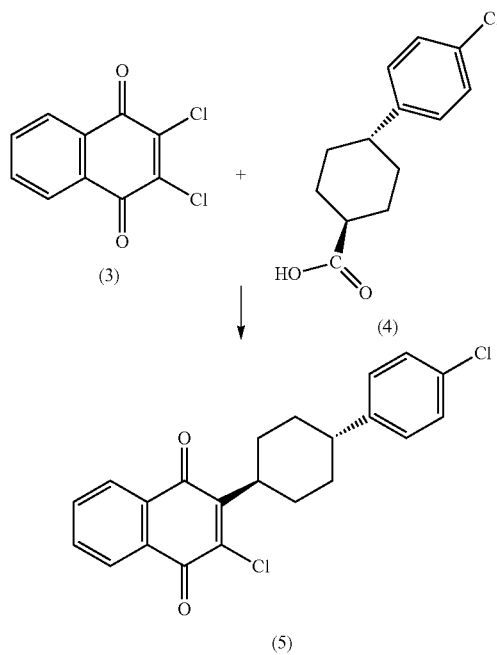

A mixture of 2,3-dichloro-1,4-naphthoquinone (5 gm), trans 4-(4-chlorophenyl)-cyclohexane-1-carboxylic acid (6.06 gm) and silver nitrate (2.47 gm) is taken in acetonitrile (60 ml) and the mixture is heated to reflux, maintaining good stirring. Then a solution of ammonium persulphate (14.23 gm) in water (77 ml) is added through a dropping funnel over a period of 1-2 hrs. The mixture refluxed for 4 hrs. Then it is cooled in ice for about 1 hr after which it is filtered. The solid is extracted with hot methylene chloride (100 ml×3). The organic layer is dried over anhydrous sodium sulphate and concentrated to get light brownish yellow solid. This on crystallization from acetonitrile afforded the trans compound as yellow crystals (1.5 gm).

Melting point, IR, NMR etc. fully matched with the product obtained from monochloro naphthoquinone. The same procedure is adopted for all the remaining five composition reported in Table-1.

Stage II. 2-[trans-4-(4-chlorophenyl)cyclohexyl]-3-hydroxy-1,4-naphthoquinone (Atovaquone) (6)

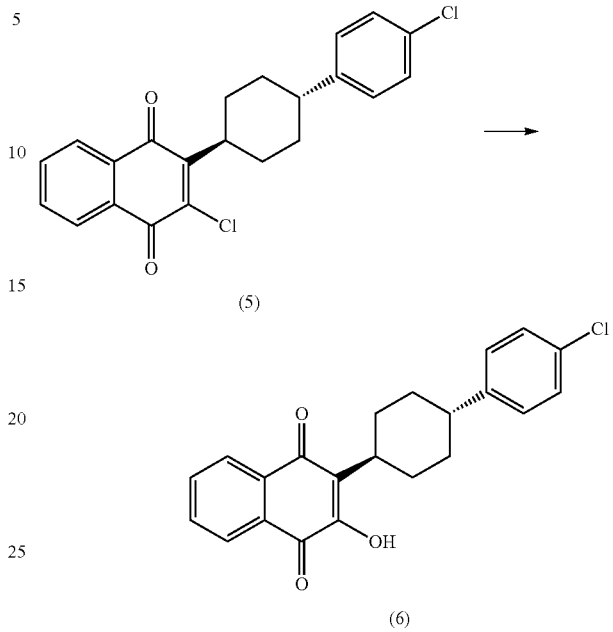

Product from stage I (1.5 gm) is taken in methanol and under stirring, potassium hydroxide (1.52 gm) dissolved in water (15 ml) is added over a period of 15-20 minutes, dropwise. The mixture is then refluxed approximately for 6-7 hrs. During this period the mixture became dark red. The mixture is then cooled in ice and concentrated hydrochloric acid (5.4 ml) is added dropwise to get yellow solid, which is filtered and washed thoroughly with water. The product after crystallization from methanol-acetic acid afforded the title compound as trans isomer (750 mg).

Melting point, IR, NMR matched with the product obtained from monochloro naphthoquinone.

EXAMPLE 2

2-[trans-4-(4-Chlorophenyl)cyclohexyl]-3-hydroxy-1,4-naphthoquinone (Atovaquone):

Stage I: Synthesis of 2-[trans-4-(4-chlorophenyl)cyclohexyl]-3-chloro-1,4-naphthoquinone (5)

A mixture of 2,3-dichloro-1,4-naphthoquinone (57.0 gm), 4-(4-chlorophenyl)-cyclohexane-1-carboxylic acid (60.0 gm) and silver nitrate (42.7 gm) is taken in acetonitrile (600 ml) and then a solution of ammonium persulphate (180.12 gm) in water (780 ml) is added. The mixture is heated to reflux, maintaining good stirring. The mixture was refluxed for 4 hrs. Then cooled in ice for about 1 hr after which it is filtered. The filtrate is kept aside for acetonitrile recovery. The solid is extracted with hot methylene chloride (100 ml×3). The inorganic salt is collected separately for recovery of silver. The organic layer is dried over anhydrous sodium sulphate and concentrated to get light brownish yellow solid (38.5 gm).

Yield %: 40%

Recovery of Acetonitrile:

Mother liquor from, stage 1 is taken in a flask for distillation. Fraction collected between 70-78 deg C is collected and analysed.

Yield: 83%

Purity by GLC: 98%

Recovery of Silver Salt and Conversion to Silver Nitrate:

The inorganics from the example 2, stage I is taken for recovery of silver. 5 g of the salt is dissolved in 70 ml of ammonia. 1.3 g of zinc dust is added to it and stirred at 40-45 deg C for 6-8 hr. Cool the mass to room temperature and filter the solid. Wash the solid with dil sulfuric acid to collect silver. This is stirred with con. Nitric acid at 90-95 deg C. for 3 hr and cooled the mass to room temperature. Filter the mass and wash with cooled methanol and dry the material.

Yield: 95%
Purity: 98%

Synthesis of 2-[trans-4-(4-chlorophenyl)cyclohexyl]-3-chloro-1,4-naphthoquinone (5) Using Recovered Acetonitrile:

A mixture of 2,3-dichloro-1,4-naphthoquinone (28.5gm), 4-(4-chlorophenyl)-cyclohexane-1-carboxylic acid (30.00 gm) and silver nitrate (21.33 g) is taken in acetonitrile(300 ml) and then a solution of ammonium persulphate (86.00 g) in water (390 ml) is added. The mixture was heated to reflux under stirring. The mixture is refluxed for 4 hrs. Then it is cooled in ice for about 1 hr after which it was filtered. The filterate is kept aside for acetonitrile recovery. The solid is extracted with hot methylene chloride (100 ml×3). The organic layer is dried over anhydrous sodium sulphate and concentrated to get light brownish yellow solid (18.5 g).

Yield %: 38.23%

Stage II:

2-[trans-4-(4-chlorophenyl)cyclohexyl]-3-hydroxy-1,4-naphthoquinone (Atovaquone) (6)

Product from stage I (37.4 gm) is taken in methanol(673.0 ml) and under stirring, potassium hydroxide (37.4 gm) dissolved in water (374.0 ml) is added over a period of 15-20 minutes. The mixture is then refluxed approximately for 6-7 hrs. During this period the mixture became dark red. The mixture is then cooled in ice and acidified with acetic acid to get yellow solid, which is filtered and washed thoroughly with water. The product on drying afforded the title compound as trans isomer (34.0 gm).

Yield: 95.5%
Purity: 99.0%.

Preparation of Polymorph Form I from N-methyl Pyrrolidone:

Atovaquone (2 g) obtained from the above process is dissolved in N-methyl pyrrolidone (10 ml) by warming The clear liquid is filtered and acetonitrile (40 ml)is added under stirring. The resulting mass is cooled to 5° C. under stirring for 0.5hr. The resulting solid is isolated by filtration. The solid is washed with acetonitrile (5m1) and dried under suction for 0.5 hr. It is further dried under vacuum to get 1.66 g of atovaquone of polymorph Form I.

Recrystallisation of Atovaquone.

(a) Recrystallisation from Dimethyl Formamide:

Atovaquone (1.00 g) is recrystallised from dimethyl formamide and isolated the material by filtration. The material is dried to get atovaquone with 2theta values as follows: 7.23, 10.74, 11.05, 11.78, 16.84, 18.06, 19.34, 19.91, 21.16, 22.85, 24.58, 24.8, 25.25, 28.46, 28.64, 29.68, 32.04

(c) Recrystallisation from Acetonitrile:

Atovaquone (1.00 g) is recrystallised from acetonitrile (80 ml) and the material is collected by filtration. Material is dried to get atovaquone of polymorph Form I.

EXAMPLE 3

Synthesis of 2-cyclohexyl-3-hydroxy-1,4-naphthoquinone (Parvaquone) (8)

Stage I. Synthesis of 2-cyclohexyl-3-chloro-1,4-naphthoquinone (7)

A mixture of 2,3-dichloro-1,4-naphthoquinone (5gm), cyclohexane carboxylic acid (2.7629 gm) and silver nitrate (2.095 gm) is taken in acetonitrile (60 ml) and the mixture is heated to reflux. Then a solution of ammonium persulphate (12.06 gm) in 77 ml of water is added through a dropping funnel over a period of 1 to 2 hrs. The mixture is refluxed for 4 hrs and cooled in ice for about 1 hr after which it is filtered. Filtrate is kept aside for acetonitrile recovery. The solid is extracted with hot methylene chloride (100 ml×3). Inorganics is kept aside for silver nitrate regeneration. The methylene chloride layer is dried over anhydrous sodium sulphate, concentrated to get light brownish yellow solid. This on crystallization from acetonitrile afforded the title compound as yellow crystals (2.5 gm). 300 MHz NMR of the compound fully agreed with the desired compound

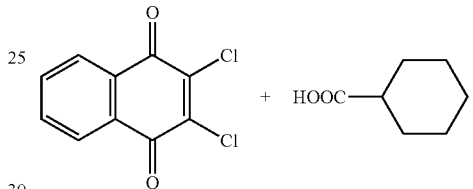

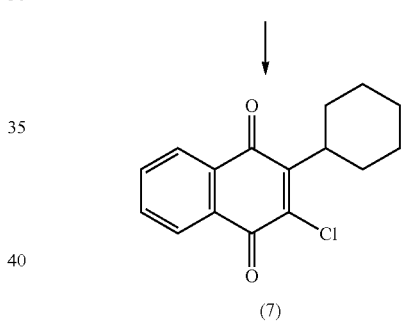

(7)

Stage II: 2-Cyclohexyl-3-hydroxy-1,4-naphthoquinone (8)

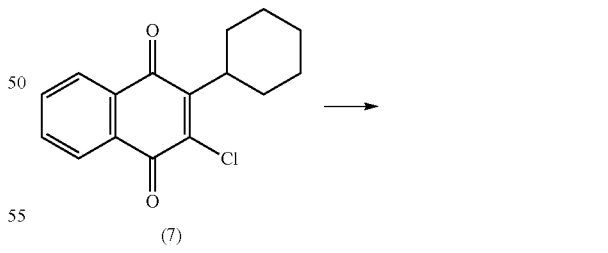

(7)

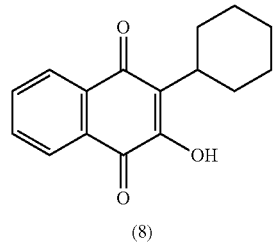

(8)

Product from stage I (1 gm) is taken in methanol and under stirring, potassium hydroxide (1.4 gm), dissolved in water (10 ml) is added over a period of 15-20 minutes dropwise. The mixture is then refluxed for 6-7 hrs, during which period, it became dark red. The mixture is cooled in ice and concentrated hydrochloric acid (3.6 ml) is added dropwise to get yellow solid, which is filtered and washed thoroughly with water. The product after crystallization from dichloromethane/hexane mixture afforded the title compound (0.75 gm), melting point 128-130° C.

EXAMPLE 4

1. 2-trans-(4-t-Butylcyclohexyl)-3-hydroxy-1,4-naphthoquinone (10)

Stage I: Synthesis of 2-trans-(4-t-butylcyclohexyl)-3-chloro-1,4-naphthoquinone (9)

A mixture of 2,3-dichloro-1,4-naphthoquinone (1.925 gm), 1-trans-(4-t-butyl-cyclohexyl)-carboxylic acid (1.806 gm) and silver nitrate (0.95 gm) in acetonitrile (25 ml) is heated to reflux with vigorous stirring whilst a solution of ammonium persulfate (5.48 gm) in water (30 ml) is added dropwise over a period of 1 to 2 hrs. The mixture is refluxed for 4 hrs and cooled in ice for about 1 hr after which it is filtered. The solid is extracted with hot methylene chloride (25 ml×3).

The methylene chloride layer is dried over anhydrous sodium sulphate and concentrated to give bright yellow solid which on crystallization from acetonitrile afforded the title compound (0.6 gm). The 300 MHz NMR fully agreed with the structure.

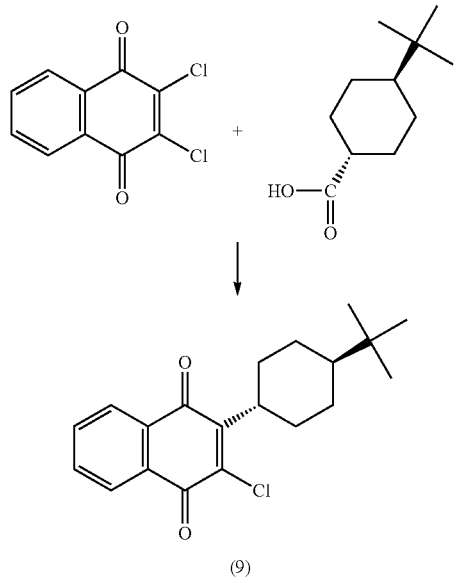

(9)

Stage II: 2-trans-(4-t-Butylcyclohexyl)-3-hydroxy-1,4-naphthoquinone (10)

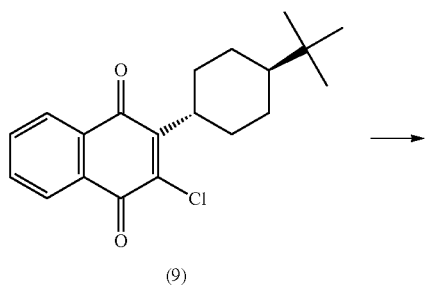

(9)

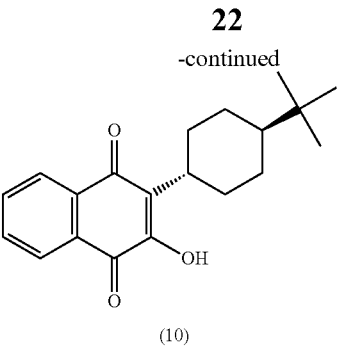

(10)

Product from stage I (0.2 gm) is taken in methanol (6 ml) and under stirring, potassium hydroxide (0.2 gm) dissolved in water (2 ml) is added over a period of 15 to 20 minutes dropwise. The mixture is then refluxed approximately for 3-4 hrs. The mixture is cooled in ice and concentrated hydrochloric acid (1 ml) is added drop wise to get yellow solid which filtered and washed thoroughly with water. The product after crystallization from dichloromethane/hexane mixture afforded the title compound (0.12 gm), melting point: 130-132° C. The structure is confirmed by 300 MHz NMR.

Although the invention has been described in terms of particular embodiments and applications, one of ordinary skill in the art, in light of this teaching, can generate additional embodiments and modifications without departing from the spirit of or exceeding the scope of the claimed invention. It should be emphasized that the above-described embodiments of the present invention, particularly any "preferred" embodiments, are merely possible examples of the invention of implementations, merely set forth for a clear understanding of the principles of the invention. Accordingly, it is to be understood that the drawings and descriptions herein are proffered by way of example to facilitate comprehension of the invention and should not be construed to limit the scope thereof.

The invention claimed is:

1. A process for the preparation of 2-cyclohexyl-1,4-naphthoquinones compounds of Formula III and its isomers,

FORMULA (III)

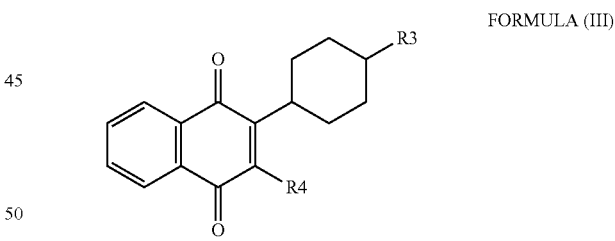

wherein, $R^3$ is selected from the group consisting of $C_{1-6}$ alkoxy; aralkoxy; $C_{1-6}$ alkyl-$C_{1-6}$ alkoxy; hydrogen; unsubstituted phenyl; phenyl substituted by one or more groups, preferably selected from halogens; $C_{1-6}$ linear or branched alkyl, halogen and perhalo-$C_{1-6}$ alkyl; $R^4$ is selected from the group comprising consisting of hydroxyl; a group $OCOR^5$, wherein $R^5$ is a $C_{1-10}$ alkyl group, a $C_{3-10}$ cycloalkyl group, a $C_{1-10}$ alkoxy group, or a phenyl or naphthyl group, each such $R^5$ group being optionally substituted e.g. by amino, mono or di-$C_{1-4}$ alkylamino, carboxy or hydroxy; a group $OR^6$ or $SR^6$, wherein $R^6$ is an optionally substituted $C_{1-10}$ alkyl, $C_{3-10}$ cycloalkyl, phenyl or naphthyl group as defined for $R^5$ or a group $NR^7R^8$, wherein $R^7$ and $R^8$ each independently represent hydrogen or $C_{1-4}$ alkyl, or the group $NR^7R^8$ which represents a 5-7 membered saturated heterocyclic ring, which may optionally contain a further heteroatom selected from nitrogen, oxygen or sulfur, comprising the steps of:
(i) condensing 2,3-dihalonaphthoquinone compounds of Formula I

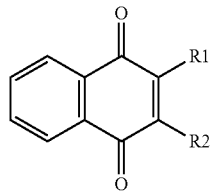

FORMULA (I)

wherein $R^1$ and $R^2$ are leaving groups selected from the group consisting of Cl, Br, I and F and the $R^1$ and $R^2$ may be the same halogen or may contain different halogen groups, or sulphonyl groups, and physiologically acceptable salts and other physiologically functional derivatives thereof, with

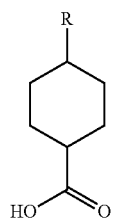

wherein R is selected from the group consisting of H,

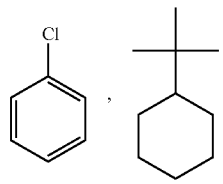

to prepare napthoquinone compounds of Formula IA;

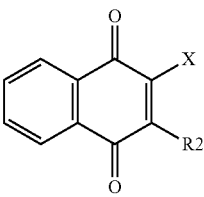

FORMULA (IA)

wherein X is any aryl, heteroaryl, alkyl, cyclohexyl, substituted cylohexyl groups;

(ii) treating napthoquinone compounds of Formula IA with base in a suitable solvent to form the 2-cyclohexyl-1,4-naphthoquinones compounds of Formula III.

2. A process for the preparation of Atovaquone of formula (6),

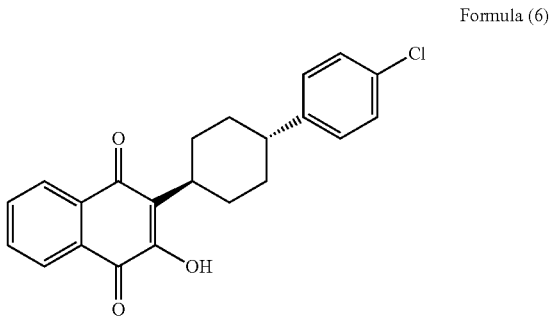

Formula (6)

comprising the steps of:
(i) condensing 2,3-dichloro-1,4-naphthoquinone of formula (3)

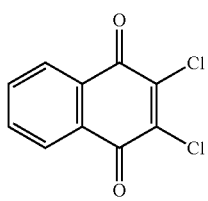

Formula (3)

with trans 4-(4-chlorophenyl)cyclohexane-1-carboxylic acid of formula (4)

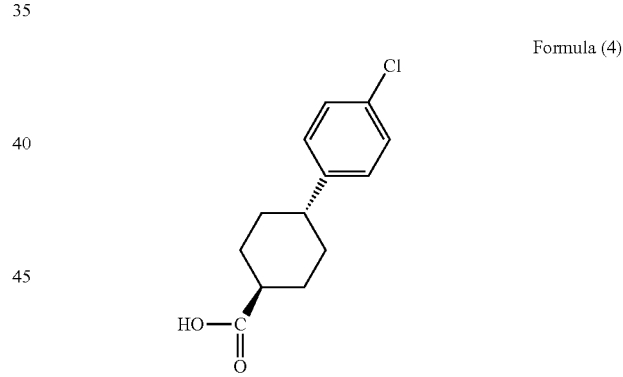

Formula (4)

in presence of silver nitrate and ammonium persulfate in a suitable solvent to provide 2-[4-(4-chlorophenyl)cyclohexyl]-3-chloro-1,4-naphthoquinone of formula (5),

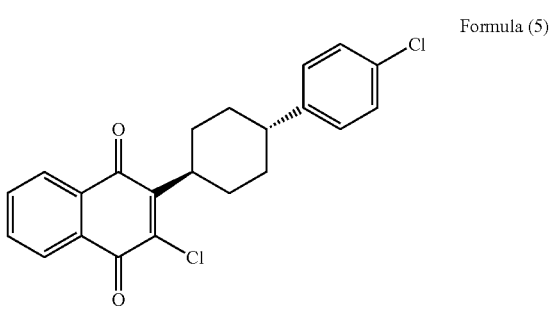

Formula (5)

(ii) treating 2-[4-(4-chlorophenyl)cyclohexyl]-3-chloro-1,4-naphthoquinone of formula (5) with a base in a solvent and followed by treatment with an acid to provide Atovaquone of formula (6).

3. The process according to claim 2, wherein the process comprises:
a) condensing 2,3-dichloro-1,4-naphthoquinone of formula (3) with trans 4-(4-chlorophenyl)cyclohexane-1-carboxylic acid of formula (4) in acetonitrile in presence of silver nitrate and ammonium persulfate in a suitable solvent to provide 2-[4-(4-chlorophenyl)cyclohexyl]-3-chloro-1,4-naphthoquinone of formula (5);
b) recovery and reuse of acetonitrile from the mother liquor
c) recovery of silver salt and further conversion to silver nitrate and its reuse;
d) treating 2-[4(4-chlorophenyl)cyclohexyl]-3-chloro-1,4-naphthoquinone of formula (5) with base in a solvent and followed by treatment with an acid to provide Atovaquone of formula (6).

4. The process according to claim 2, wherein the acid used for acidification is selected from an organic acid selected from the group consisting of aliphatic acids and aromatic acids, sulphonic acids or mixtures thereof.

5. The process according to claim 4, wherein the acid is acetic acid.

6. The process according to claim 2, wherein the atovaquone is dissolved in N-methylpyrrolidone and precipitated by adding acetonitrile to obtain atovaquone polymorph Form I.

7. The process according to claim 2, wherein the process comprises using silver nitrate and 2,3-dihalonaphthoquinone in the molar ratio of 0.8:1 to 2:1 to provide atovaquone form I of at least 99% purity.

8. A process for the preparation of Parvaquone of formula (8),

Formula (8)

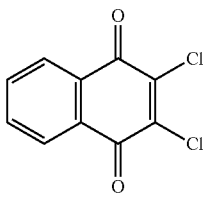
(8)

which comprises the steps of (i) condensing 2,3-dichloro-1,4-naphthoquinone of formula (3)

Formula (3)

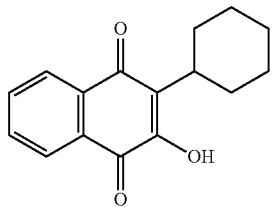

with 4-cyclohexane carboxylic acid in presence of silver nitrate and ammonium persulfate in a suitable solvent to provide 2-Cyclohexyl 3-chloro 1,4-naphthoquinone of formula (7), Formula (7)

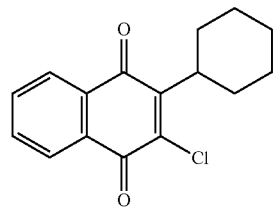

(ii) treating 2-cyclohexyl-3-chloro-1,4-naphthoquinone of formula (5) with base in a solvent and followed by treatment with an acid to provide Parvaquone of formula (8).

9. A process for the preparation of 2-trans-(4-t-Butylcyclohexyl)-3-hydroxy-1,4-naphthoquinone of formula (10), Formula (10)

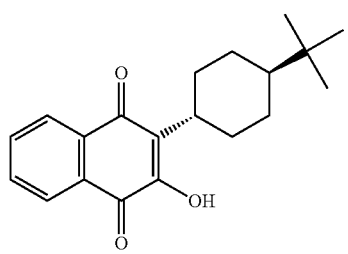

which comprises the steps of (i) condensing 2,3-dichloro-1,4-naphthoquinone of formula (3)

Formula (3)

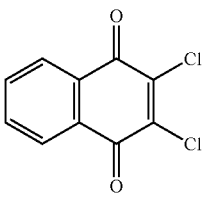

with 1-trans-(4-t-butyl-cyclohexyl)-carboxylic acid in presence of silver nitrate and ammonium persulfate in a suitable solvent to provide 2-trans-(4-t-butylcyclohexyl)-3-chloro-1,4-naphthoquinone of formula (9), Formula (9)

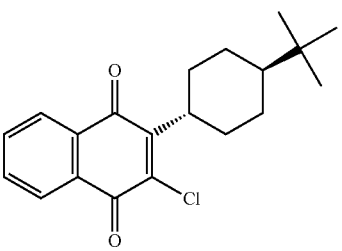

(ii) treating 2-trans-(4-t-butylcyclohexyl)-3-chloro-1,4-naphthoquinone of formula (9) with base in a solvent and followed by treatment with an acid to provide 2-trans-(4-t-butylcyclohexyl)-3-hydroxy-1,4-naphthoquinone of formula (10).

10. The process according to claim 1, wherein the solvent is selected from the group consisting of substituted, unsubstituted, cyclic, bicyclic, saturated, or unsaturated, straight or branched hydrocarbon but not limited to aliphatic or aromatic hydrocarbon, having $C_6$-$C_{10}$ atoms, water, aliphatic nitrile, alcohols, ketones, esters, ethers and chlorinated solvents, or mixtures thereof.

11. The process according to claim 10, wherein the solvent is selected from the group consisting of hexane, toluene; ethyl acetate, propyl acetate, isopropyl acetate, butyl acetate and isobutyl acetate; water; aliphatic acetonitrile and propionitrile; methanol, ethanol and isopropanol; acetone, methyl ethyl ketone, methyl isobutyl ketone and diethyl ketone; tetrahydrofuran and dioxane; and methylene chloride, chloroform, carbontetrachloride and ethylene dichloride; or mixtures thereof.

* * * * *